United States Patent [19]
Cook et al.

[11] Patent Number: 5,997,500
[45] Date of Patent: Dec. 7, 1999

[54] PNEUMATICALLY OPERATED VETERINARY PELLET IMPLANTER

[75] Inventors: David L. Cook, Harrisonville, Mo.; Michael L. Grimm, Kansas City, Kans.; Michael J. Zalta, Richardson, Tex.; C. Louis Grimm, deceased, late of Shawnee, Kans., by Joan Grimm, heir

[73] Assignee: Ivy Animal Health, Inc., Overland Park, Kans.

[21] Appl. No.: 09/062,826

[22] Filed: Apr. 20, 1998

[51] Int. Cl.⁶ .................................................. A61M 31/00
[52] U.S. Cl. ........................... 604/60; 604/62; 604/141; 604/143
[58] Field of Search ................................. 604/57, 59, 60, 604/61, 62, 70, 1, 30, 131, 140, 141, 143, 147, 209, 207

[56] References Cited

U.S. PATENT DOCUMENTS

| | | |
|---|---|---|
| 4,108,176 | 8/1978 | Walden . |
| 4,177,810 | 12/1979 | Gourlandt . |
| 4,327,724 | 5/1982 | Birk et al. . |
| 4,717,384 | 1/1988 | Waldeisen . |
| 4,784,640 | 11/1988 | Johnson et al. ........................... 604/62 |
| 4,790,823 | 12/1988 | Charton et al. . |
| 4,861,340 | 8/1989 | Smith et al. . |
| 4,943,294 | 7/1990 | Knapp ..................................... 606/117 |
| 5,015,237 | 5/1991 | Kleinwolterink, Jr. et al. . |
| 5,522,797 | 6/1996 | Grimm ..................................... 604/61 |
| 5,827,297 | 10/1998 | Boudjema ................................ 606/133 |

*Primary Examiner*—Wynn Wood Coggins
*Assistant Examiner*—LoAn H. Thanh
*Attorney, Agent, or Firm*—Litman, Kraai & Brown, L.L.C.; John C. McMahon

[57] ABSTRACT

A pneumatically operated veterinary medicinal pellet implanter utilizes pressurized air to drive an impeller for dispensing medicinal pellets through a needle on an end of the implanter and into a cavity created by the needle under the skin of an animal to be treated. The pressurized air source may also be utilized to retract the impeller after dispensing of the pellets. The impeller is part of a piston slidingly secured within a pneumatic cylinder. Pressurized air is selectively and alternatingly supplied to the front and rear and rear of the cylinder for advancing the impeller between retracted and extended positions respectively. The pressure of the air supplied to the rear of the cylinder for driving the impeller is reduced relative to the pressure of the air supplied to the front of the cylinder for retracting the impeller.

12 Claims, 4 Drawing Sheets

PNEUMATICALLY OPERATED VETERINARY PELLET IMPLANTER

BACKGROUND OF THE INVENTION

This invention relates to pellet implanters and in particular to hand held implanters for implanting medicinal pellets and the like in animals.

Pellet implanters are widely used in livestock handling operations to insert solid or semisolid medicaments such as growth stimulating hormones into animals to be treated. Pellets containing growth stimulating hormone are typically injected into the ears of domesticated animals since the ears are commonly discarded in the slaughtering process thereby preventing unabsorbed residues from ending up in food products intended for human or domestic animal consumption.

Typical implanter devices comprise hand held instruments built of a size consistent with the size of the animal. The pellets are normally implanted while an animal is confined in a chute. An ear is grasped in one hand, and an implanter device having a large bore hypodermic needle is used to puncture the hide to enable a pellet dose to be injected between the hide and the next layer of tissue in the ear. The implanting must be done carefully to ensure that the pellets are properly placed and that no pellet remains in the puncture in the hide, which could result in an infection. At the same time, the procedure must be carried out quickly since the animals are not entirely cooperative and may shake their heads to free the held ear.

Further complicating matters is that other procedures may be occurring at the same time as the implanting operation while the animal is confined, such as ear tagging, branding, veterinary inspections or procedures, or the like, which may further excite the animal.

The great majority of implanter devices employ manual gripping force on a trigger and a hand grip of such a device to propel an impeller through a pellet holding device or a magazine to drive the pellets through the needle and into the space formed by operation of the trigger to return the impeller to its retracted position when the trigger is released. With such an arrangement, pellet implanting is complicated by the need to coordinate withdrawal of the needle as the pellets exit the needle. Such complexity of motion coupled with fatigue from using grip strength to eject the pellets can result in mistakes, such as lodging a pellet in the hide puncture or some of the pellets being ejected onto the ground.

A number of implanter devices use multiple pellet dose magazines to hold a plurality of pellet doses. Each pellet dose usually consists of a plurality of small pellets of a measured drug dosage which are positioned in an in-line orientation within a cylindrical chamber of the magazine. The magazine is a strip having a plurality of such chambers arranged in parallel relation, such as by being connected by webs between the chambers. Although some implanters are known to have magazines which advance to the next magazine chamber each time an implant operation occurs, many implanters require manual advancing of their magazines. Such manual advancing of the pellet magazine requires that the person performing the implanting operation remember to advance the magazine after each operation. If the magazine is not advanced, no pellets will be injected.

U.S. Pat. No. 5,522,797 discloses an implanter in which the impeller is manually retracted against the driving force of a spring and then locked in position with a latch mechanism, thereby storing the spring force. Squeezing or pivoting of an associated trigger, releases the latch mechanism which resiliently drives the impeller through an aligned magazine chamber and propels the pellet or pellets in the magazine into the needle. As the needle is withdrawn from the portion of the animal into which it has been inserted, the pellets are urged out of the end of the needle and into the hole formed by the needle. Although the implanter disclosed in U.S. Pat. No. 5,522,797 overcomes many of the problems associated with prior art implanters, the user must still manually retract the impeller after each use which can slow down the process of implanting medicaments in a large number of animals such as may be necessary in large feed lots.

There remains a need for an implanter which permits rapid, successive implantation of medicaments in a large number of animals with minimal manual effort.

SUMMARY OF THE INVENTION

The present invention comprises a pneumatically operated veterinary medicinal pellet implanter. The implanter is connected to a pressurized air source and the pressurized air is utilized to drive an impeller for dispensing the medicinal pellets through a needle on an end of the implanter and into a cavity created by the needle under the skin of the animal. The pressurized air source may also be utilized to retract the impeller after dispensing of the pellets. Utilization of pressurized air to drive and retract the impeller minimizes the manual activity required to operate the implanter thereby increasing implantation speed and accuracy and reducing fatigue in the arm muscles of the person administering the implanted drugs.

The implanter apparatus of the present invention includes a housing with a tubular main housing section, a magazine housing depending from the main housing at a front end thereof, and a grip housing depending from the main housing in spaced relation behind the magazine housing. An air cylinder is mounted longitudinally within the main housing rearward of the magazine housing. The impeller is slidingly mounted within the air cylinder such that a front end of the impeller extends through a front end of the cylinder in alignment with a magazine chamber of a magazine positioned in the magazine housing and in alignment with the bore of a needle mounted on the front end of the main housing of the implanter.

An air supply conduit assembly is formed within the main housing and the grip housing. A flexible air supply hose is connectable to the air supply conduit assembly at the bottom of the grip housing and an opposite end of the air supply hose is connected to a source of pressurized air. In a preferred embodiment, pressurized air is supplied to the air supply conduit assembly preferably at a pressure of approximately 110 psig.

The air supply conduit is split in the grip housing into two main branches, a high pressure branch and a reduced pressure branch. The high pressure branch supplies pressurized air, at the inlet pressure (i.e. 110 psig), to a front end of the air cylinder, and the reduced pressure branch supplies pressurized air at a reduced pressure to a rear end of the air cylinder. A regulator positioned on the reduced pressure branch reduces the pressure of the air on the downstream side thereof to a selected pressure, preferably approximately 30 psig.

A plunger valve, actuated by a trigger on the grip housing, is connected to the high pressure branch upstream of the air cylinder. Squeezing or pivoting of the trigger rearward into the grip housing, closes the plunger valve, cutting off the supply of high pressure air to the front of the air cylinder. A spring in the grip housing biases against an inner surface of the trigger so as to urge the trigger outward such that the plunger valve is normally maintained in an open alignment, except when the trigger is squeezed.

A second valve is positioned on the reduced pressure branch, between the regulator and rear end of the air cylinder. The second valve is actuated by a stream of high pressure air supplied by a spur of the high pressure branch, which splits off of the high pressure branch downstream of the plunger valve and which extends into the second valve. When the trigger is not retracted, such that the plunger valve is open, the high pressure air from the high pressure branch closes the second valve cutting off the supply of reduced pressure air to the rear of the air cylinder. The high pressure air, supplied to the front of the air cylinder acts upon a front face of a washer mounted on a rear end of the impeller thereby urging the impeller rearward into a retracted alignment.

When the trigger is pivoted into the grip housing, the plunger valve is closed cutting off the supply of high pressure air to the front of the air cylinder and to the second valve. Cutting off of the high pressure air to the second valve opens the second valve thereby supplying reduced pressure air to the rear of the air cylinder which acts upon a rear surface of the impeller washer driving the impeller forward. As the impeller is driven forward, a front end of the impeller passes through the aligned magazine chamber, driving the pellets contained therein into the bore of the needle. The pressure of the air in the reduced pressure branch is set sufficiently low such that the advancement of the impeller does not crush the pellets or cause further separation of the animal skin or cartilage by ejection of the pellets. Instead, the impeller advances the pellets into the bore of the needle, and then as the needle is withdrawn the impeller is further advanced by the reduced pressure air such that the pellets are advanced out of the needle bore and into the cavity in the animal created by the needle.

Once the needle is fully withdrawn and the pellets are ejected, the trigger is released, opening the plunger valve to supply high pressured air to the front of the air cylinder and closing the second valve shutting of the supply of reduced pressure air to the rear of the air cylinder, such that the high pressured air acts on the front of the air cylinder washer driving the impeller rearward into a retracted position.

The pellet magazine is formed by a strip of parallel pellet chambers connected by web sections between the chambers. The ends of the magazine are cooperatively formed so that the top end of one magazine can removably attach to the bottom end of another. The magazine is fed through a slot or channel formed in the magazine housing and extending from the bottom to the top thereof. The magazine is automatically advanced one chamber for each reciprocation of the trigger.

A magazine feed pawl is mounted on an upper end of the trigger generally at the pivot point thereof and generally extends perpendicular to the trigger. The pawl extends forward of the trigger and within the main housing with a tip of the pawl extending between adjacent chambers of the magazine. As the trigger is pivoted into the grip housing, the pawl rotates downward such that the tip of the pawl slips over the next magazine chamber. When the trigger is released and biased away from the grip housing by the trigger spring, the tip of the pawl engages a lower surface of the magazine chamber and advances the magazine upward to align the next chamber with the needle and the impeller.

To use the implanter, an operator simply sticks the needle into the hide of the animal to be treated, squeezes the trigger which causes the impeller to be driven forward to eject the pellets in the aligned magazine chamber into the needle, withdraws the needle while holding the trigger in the retracted position such that the impeller pushes the pellets from the needle and into the cavity formed by the needle in the animal, and then releases the trigger which causes the impeller to retract and advances the next magazine chamber into alignment with the impeller and the needle. The needle may be quickly sanitized and the implanter is then ready for the next implantation with minimal effort by the operator.

OBJECTS AND ADVANTAGES OF THE INVENTION

Objects and advantages of the invention include: providing an implanter which requires minimal manual action to operate, to provide an implanter which permits rapid and accurate delivery of medicine to animals; to provide an implanter which utilizes pressurized air to drive an impeller for injecting medicinal pellets into an animal; to provide such an implanter which utilizes pressurized air to retract the impeller, to provide such an implanter wherein the impeller is driven forward for ejecting pellets upon retraction of a trigger on a grip handle of the implanter; to provide such an implanter wherein the impeller is automatically retracted upon release of the trigger; to provide such an implanter wherein the pellets are ejected from a magazine containing multiple magazine chambers and wherein the next magazine chamber is advanced into alignment with the impeller upon release of the trigger; and to provide such an attachment which is particularly well adapted for its intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is a schematic diagram of the pneumatic assembly of the pellet implanter of the present invention.

DETAILED DESCRIPTION OF THE INVENTION

Figure 1:
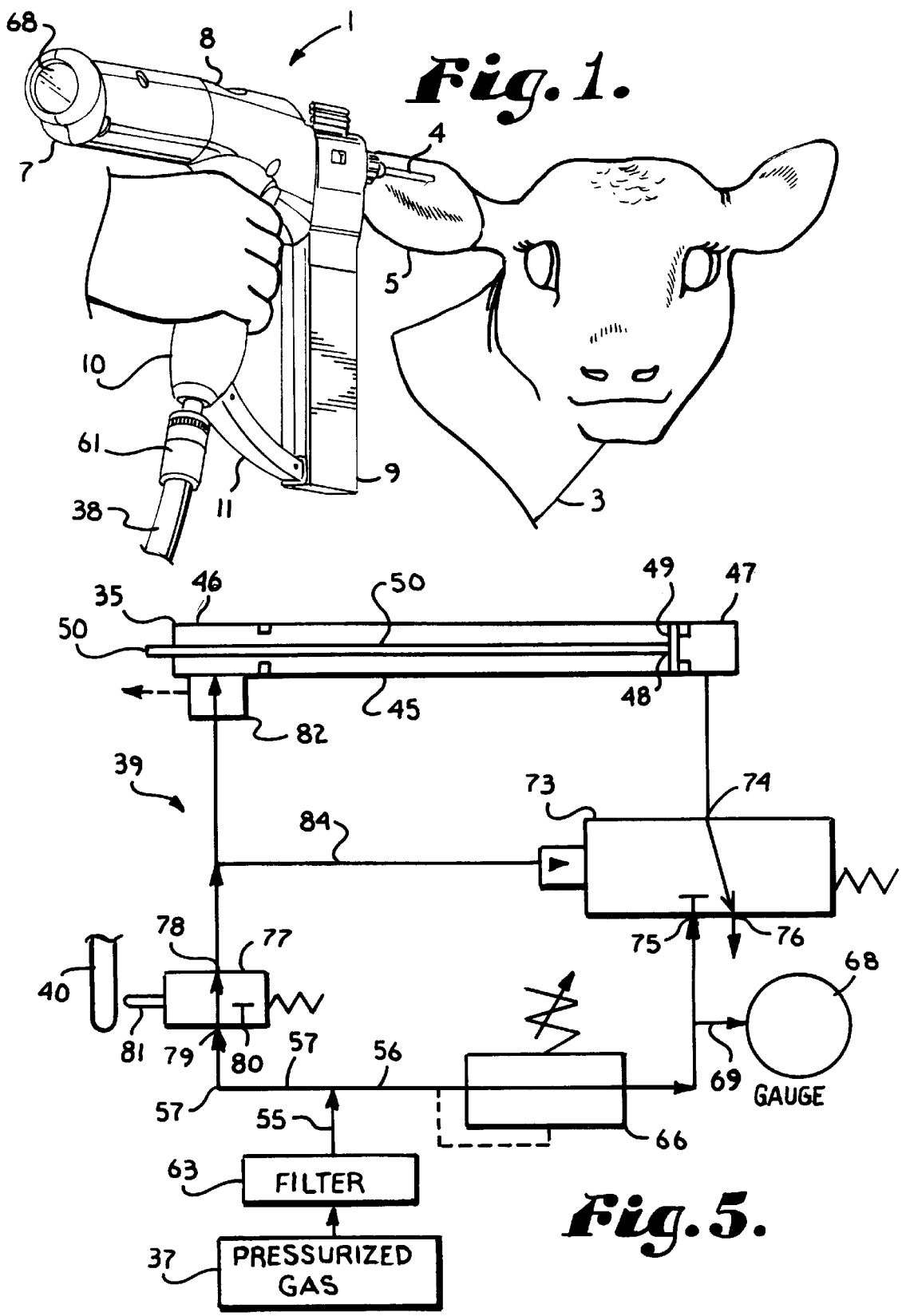
FIG. 1 is a perspective view of a pneumatically operated veterinary pellet implanter of the present invention shown in use.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 refers to a pneumatically operated veterinary pellet implanter of the present invention. The implanter 1 is used to implant solid form drugs, such as pellets 2 (see FIG. 3), into an animal 3 through a hypodermic needle 4 such as through an ear 5 of the animal 3.

Figure 2:
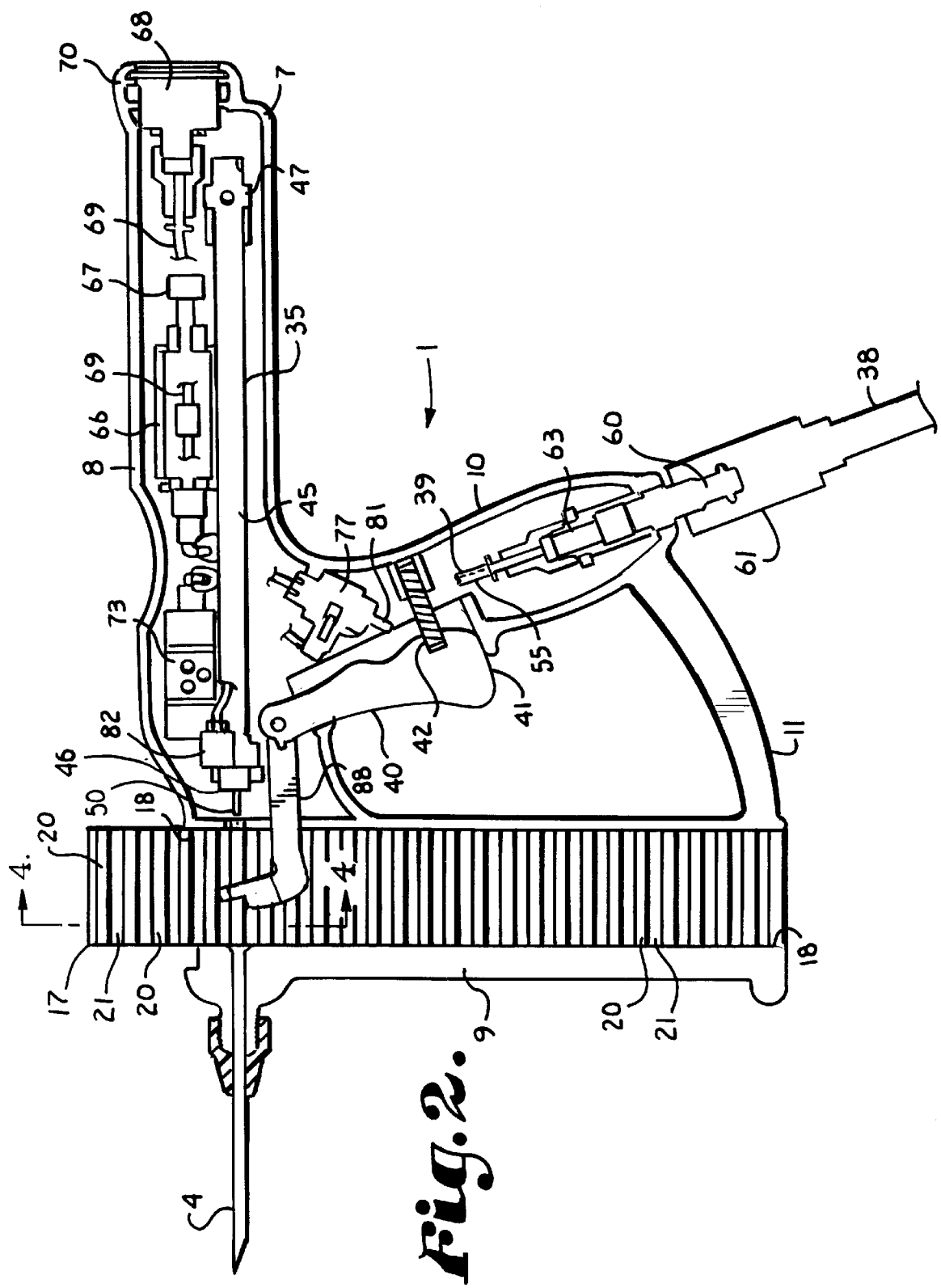
FIG. 2 is an enlarged side elevational view of the implanter as shown in FIG. 1 with a portion of the housing removed to show interior detail and with portions broken away for clarity and showing an impeller in a retracted position.

Referring to FIGS. 1 and 2, the implanter apparatus 1 generally includes a housing 7 having a barrel portion 8, a magazine portion 9 depending from the barrel portion 8 at a front end thereof, and a grip portion 10 depending from the barrel portion 8 in spaced relation behind the magazine portion 9. A strut 11 connects the magazine portion 9 to the grip portion 10 at lower ends thereof. The needle 4, having needle bore 12 extending therethrough, is removably mounted to a front end of the barrel portion 8 generally along a longitudinal axis thereof.

Figure 3:
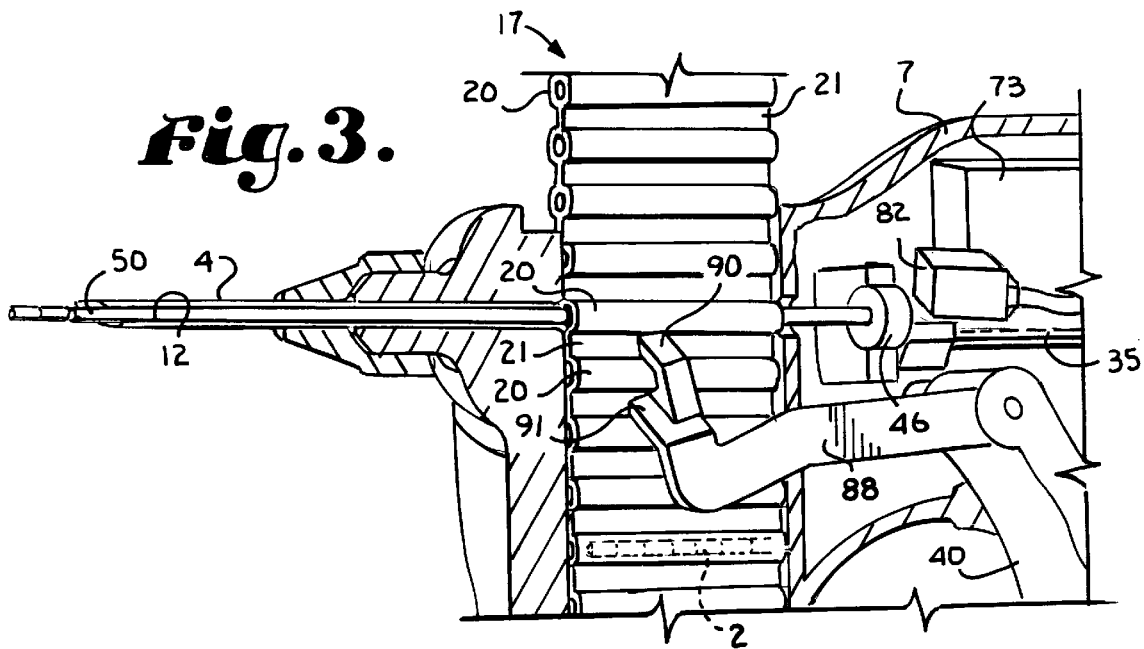
FIG. 3 is an enlarged and fragmentary perspective view of the implanter similar to FIG. 2 showing the impeller in an extended position and ejecting pellets from the implanter.
Figure 4:
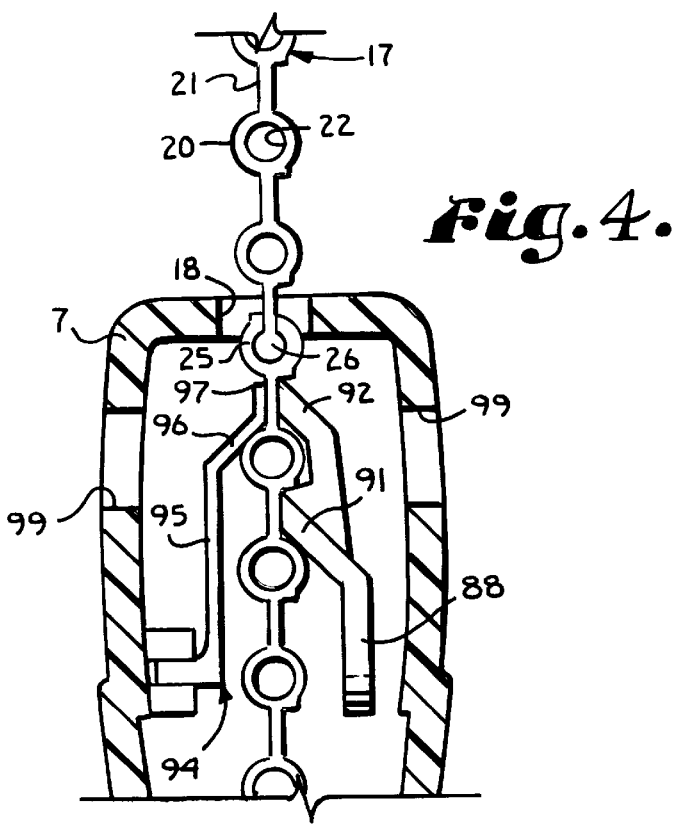
FIG. 4 is an enlarged and fragmentary cross-sectional view taken generally along line 4—4 of FIG. 2 (without a portion of the housing removed).

A pellet magazine or magazine strip 17, as best seen in FIGS. 3 and 4 is slidingly securable within a slot 18 extending through the magazine portion 9 of the housing 7. The magazine strip 17 comprises a plurality of cylindrical pellet casings 20 arranged in parallel and slightly spaced apart relation and connected together by intervening webs 21 extending between adjacent casings 20. A pellet chamber or bore 22 is formed in each of the casings 20 for receiving one or a plurality of medicinal pellets 2 therein. Each casing 20 may have internal formations (not shown) extending into the chamber 22 to retain the pellets 2 therein.

A plurality of strips 17 can be connected together in end to end relation to increase the implanting capacity without reloading. Each strip 17 has a connector clamp 25 at a top end and a cooperating connector bead 26 formed at a lower end on a terminating web 21. The top side of the connector clamp 25 is split to receive the bead 26 and associated web 21 of another strip 17. The implanter apparatus may include a magazine drum (not shown) which may be removably secured to the magazine portion 9 of the housing 7. A plurality of end to end connected strips 17 can be rolled up into the drum and fed upwardly through the magazine slot 18. As the pellets 2 in an individual magazine strip 17 are exhausted, the empty strip 17 can be detached from the next adjacent strip 17 and discarded. Each magazine strip 17 may be provided with a key tab which matches a corresponding key notch (not shown) in a magazine entry port of slot 18 and a similar key notch (not shown) in a magazine exit port of slot 18 to properly orient the magazine 17 within the slot 18.

A pneumatic impeller assembly 35 is mounted within the barrel portion 8 of the housing 7 rearward of the magazine slot 18 as generally shown in FIG. 2. The pneumatic impeller assembly 35 is connected to a source of pressurized gas 37 by a flexible supply line 38 and a conduit assembly 39 within the housing 7. A trigger 40 is pivotally mounted at an upper end to the housing 7 such that the trigger is generally pivotable within a trigger slot 41 in the grip portion 10 of the housing 7 for use in selectively controlling the delivery of pressurized gas to the impeller assembly 35 as discussed in more detail below. A trigger spring 42 secured to and within the grip portion 10 of the housing 7 biasingly engages the trigger 40 from the rear and proximate a lower end thereof so as to normally bias the trigger 40 out of the trigger slot 41.

The impeller assembly 35, as shown schematically in FIG. 5, includes an air cylinder, barrel or canister 45 having a front end 46 and a rear end 47 and a piston 48 mounted for reciprocal motion within the cylinder 45. The piston 48 includes a piston head 49 and a piston rod or impeller 50. The impeller 50 extends forwardly of the piston head 49 and through an opening in the front end 46 of the cylinder 45. The impeller assembly 35 is mounted in the barrel portion 8 of housing 7 such that the impeller 50 extends in axial alignment with the needle 4. The impeller 50 is slidingly advanceable within the cylinder 45 between a retracted position wherein the piston head 49 is positioned proximate the rear end 47 of the cylinder 45 with substantially all of the impeller 50 being positioned within the cylinder 45, and an extended position wherein the piston head 49 is positioned proximate the front end 46 of the cylinder 45 with a substantial portion of the impeller 50 extending out of the cylinder 45 such that a front end of the impeller 50 extends completely through the needle 4.

The conduit assembly 39, as shown diagrammatically in FIG. 5, includes a trunk line 55 which splits into a first branch or low pressure branch 56 and a second branch or high pressure branch 57. The low pressure branch 56 is connected at a distal end thereof to the rear end 47 of the air cylinder 45, and the high pressure branch 57 is connected at a distal end thereof to the front end 46 of the air cylinder 45.

A male connector 60, of a quick coupling assembly as shown in FIG. 2, is secured on an outer end of the trunk line 55 and extends out of the bottom of the grip portion 10 of the housing 7. The male connector 60 is removably securable to a female connector 61, of a quick coupling assembly, on an end of the flexible supply line 38. An opposite end of the supply line 38 is connected to the source of pressurized gas 37. The pressurized gas may comprise pressurized air supplied from a compressor or a compressed air canister. The pressurized gas could also be supplied from a compressed gas cartridge removably attachable directly to the male connector 60, eliminating the need for the flexible supply line 38 and making the implanter 1 more portable. It is foreseen that a wide range of gasses, including but not limited to air, carbon dioxide and nitrogen could be utilize as the pressurized gas and that these gasses could be provided from a wide variety of sources, now known or later developed.

An air filter and dryer 63 is flow connected to the trunk line 55 to clean and dry the compressed gas flowing through the conduit assembly 39.

In a preferred embodiment, pressurized air is supplied from its source 37 at approximately 110 psig. A pressure control mechanism or pressure regulator 66 is flow connected to the low pressure branch 56. The pressure regulator 66 is adapted to reduce the pressure in the low pressure branch 56 on the downstream side of the regulator 66 to a selected pressure, which in a preferred embodiment is approximately 30 psig. An adjustment knob 67 on the regulator 66 allows the set point for the outlet pressure of the regulator 66 to be adjusted. In the preferred embodiment, the adjustment knob 67 is not accessible when the implanter 1 is assembled although it is foreseen that in alternative embodiments, access may be provided to the adjustment knob 67 when the implanter 1 is assembled.

A pressure gauge 68 is flow connected to the low pressure branch 56 downstream of the regulator 66 via a gauge branch 69 extending off of the low pressure branch 56. The pressure gauge 68 is mounted in a rear end 70 of the barrel portion 8 of the housing 7 to permit visual verification of the air pressure in the low pressure branch 56 downstream of the regulator 66.

A first valve 73 is flow connected to the low pressure branch 56 downstream of the regulator 66 and gauge branch 69. An Eagle 4-way air piloted valve sold by Clippard Instrument Laboratories, Inc. ("Clippard"), with an outlet port blocked off to obtain the desired functionality of a three-way valve, may be used as the first valve 73. The first valve 73 is advanceable between an open condition and a closed condition but is normally maintained in the closed condition as shown in FIG. 5 and as discussed in more detail below. When the first valve 73 is advanced to the open condition, an outlet 74 of valve 73 is flow connected to an inlet 75 of valve 73 to open an air flow passageway through the low pressure branch 56 of the conduit assembly 39 such that pressurized air, at the reduced pressure, is supplied to the air cylinder 45 at the rear end 47 thereof. When the first valve 73 is advanced to the closed condition, the outlet 74 is flow connected to a vent opening 76 of valve 73 such that the air flow passageway through the low pressure branch 56 is closed and the portion of the low pressure branch 56 extending between the first valve 73 and the rear end 47 of the air cylinder 45 is vented or opened to the atmosphere through the first valve 73.

A second valve or plunger valve 77, such as a MAVO-3 normally open 3-way spool valve of Clippard, is flow connected to the high pressure branch 57. The second valve 77 is advanceable between a normally open condition and a closed condition by compression of a plunger 81 on the valve 77. When the second valve 77 is in the open condition, an outlet 78 thereof is flow connected to an inlet 79 thereof such that an air flow passageway through the high pressure branch 57 is open and pressurized air, at the inlet pressure, i.e. 110 psig, is supplied to the air cylinder 45 at the front end 46 thereof. When the second valve 77 is advanced to the closed condition by application of a compressive force on the plunger 81, the outlet 78 of second valve 77 is flow connected to a vent opening 80 of the second valve 77 such that the air flow passageway through the high pressure branch 57 is closed and the portion of the high pressure branch 57 extending between the second valve 77 and the front end 46 of the air cylinder 45 is vented or opened to the atmosphere through the second valve 77. Release of the compressive force on the plunger 81 allows the second valve 77 to advance back to the open condition.

A poppet type quick exhaust valve 82, such as a MEV-2 Quick Exhaust Valve of Clippard, is flow connected to the high pressure branch 57 proximate the front end 46 of the air cylinder 45. The quick exhaust valve 82 permits rapid venting of the high pressure branch 57 between the front end 46 of the air cylinder 45 and the second valve 77 when the second valve 77 is advanced to the closed condition and the high pressure branch 57 is vented to atmosphere through the second valve 77.

A spur 84 off of the high pressure branch 57 extends from the high pressure branch 57, downstream of the second valve 77, to the first valve 73. The supply of pressurized gas, at the higher pressure, i.e. 110 psig, to the first valve 73 through the spur 84 advances the first valve 73 to the closed condition. When the supply of pressurized gas at the higher pressure is cut off and the spur 84 is vented to atmosphere by closing of the second valve 77, the supply of pressurized gas from the low pressure branch 56 into the first valve 73 advances the first valve 73 to the open condition. Therefore, advancement of the second valve 77 from the open to the closed condition, advances the first valve from the closed to the open condition and vice versa.

The second valve 77 is positioned within the grip portion 10 of the housing 7 behind the trigger 40 with the plunger 81 of the second valve 77 extending toward the trigger 40. An end of the plunger 81 is spaced slightly behind a rear surface of the trigger 40, such that the trigger 40 is pivoted from its fully extended position rearward into the trigger slot 41 approximately five degrees before engaging the plunger 81. Further rearward pivoting of the trigger 40 compresses the plunger 81 advancing the second valve 77 from the open to closed condition. After initial engagement of the plunger 81, the trigger 40 can rotate approximately five degrees further rearward before the plunger 81 is completely compressed.

A magazine feed pawl 88 is secured to and extends forwardly from the trigger 40 generally from the pivot point thereof. The pawl 88 extends through the barrel portion 8 of the housing 7 and into the magazine portion 9 and across a portion of the magazine slot 18. A distal end 89 of the pawl 88 curves inward and upward and includes a pair of spaced apart tips, upper pawl tip 90 and lower pawl tip 91, extending between adjacent pellet casings 20 of a pellet magazine strip 17 secured within the magazine slot 18.

When the trigger 40 is in its fully extended orientation, the bottom tip 91 of the pawl 88 extends just below a pellet casing 20 positioned in axial alignment with the needle 4 and the impeller 50, and the top tip extends just below the previous casing 20 positioned thereabove. The pawl 88 is formed from plastic and is relatively thin along its main length to permit side to side flexing.

A stop 94 extends into the magazine slot 18 from the magazine housing 9 on a side opposite of a magazine strip 17 from the pawl 88. The stop 94 includes a flexible lower portion 95, an angled cam surface 96 and a magazine engaging portion 97 at an upper end thereof. The angled cam surface 96 angles inward toward the magazine strip 17 such that the magazine engaging portion 97 extends between successive pellet casings 20 and an upper surface of the magazine engaging portion engages the lower surface of a pellet casing 20 to prevent the strip from advancing downward within the magazine slot 18.

When the trigger 40 is pivoted rearward, the pawl 88 is rotated downward and the upper pawl tip 90 slips past the pellet casing 20 aligned with the needle 4 and impeller 50, and the lower pawl tip 91 slips past the next successive casing 20 positioned therebelow. When the trigger 40 is released so as to be pivoted forward and out of the trigger slot 41 by spring 42, the pawl 88 rotates upward such that the upper pawl tip 90 and the lower pawl tip 91 engage lower surfaces of the respective pellet casings 20 over which the were just advanced so as to drive the magazine strip 17 upward until what was the next successive casing 20 is now axially aligned with the needle 4 and impeller 50. As the magazine strip 17 is advanced upward, the upper surface of a pellet casing 20 engages the angled cam surface 96 of stop 94 thereby advancing the magazine engaging portion 97 of the stop from between successive pellet casings 20 thereby permitting upward advancement of the magazine strip 17. As that casing 20 passes past the magazine engaging portion 97 of the stop 94, the magazine engaging portion springs back in between the next successive pair of pellet casings 20.

Operation

To use the implanter 1, an operator first connects the implanter to the source of pressurized gas 37 and threads a pellet magazine strip 17 through the magazine slot 18 to position a pellet casing 20 in axial alignment with and between the needle 4 and the impeller 50. At this point, the trigger 40 is left in the extended position such that the second valve 77 is in the open condition and the first valve 73 is in the closed condition and pressurized air at approximately 110 psig is supplied through the front end 46 of the cylinder 45 so as to act against a front surface of the piston head 49 maintaining the piston head 49 to the rear end 47 of the cylinder 45 and the impeller 50 in a retracted alignment therewith.

Without squeezing the trigger, the operator then inserts the needle 4 through the hide of the animal 3 and between the hide and the next layer of tissue to form a cavity therebetween. With the needle 4 extending into the animal 3, the operator squeezes or pivots the trigger 40 rearward and then while holding the trigger 40 in the retracted position, the operator withdraws the needle 4. Once the needle 4 is fully withdrawn, the operator releases the trigger 40.

As discussed above, pivoting the trigger 40 rearward, compresses the plunger 81 which changes the condition of the second valve 77 from open to closed and cocks the pawl 88 relative to the magazine strip 17. Advancement of the second valve 77 to the closed condition, cuts off the supply of high pressure air to the front end 46 of the cylinder 45 and to the first valve 73, and also vents to atmosphere the portion of the high pressure branch 57 (including spur 84) downstream of the second valve 77. Cutting off the supply of high pressure air to the first valve 73 and venting the high pressure branch 57 to atmosphere, allows the reduced pressure air in the low pressure branch 56 to advance the first valve 73 to the open condition so as to supply reduced pressure air to the cylinder 45 at the rear end 47. The reduced pressure gas acts upon a rearwardly facing surface of the piston head 49 driving the piston head 49 toward the front end 46 of the air cylinder 45 and driving the front end of the impeller 50 through the pellet chamber 22 of the aligned pellet casing 20. The impeller 50 engages the pellets 2 in the casing 20 and pushes the pellets 2 into the aligned needle bore 12. The pressure in the low pressure branch 56 is selected to provide sufficient force to quickly advance the pellets 2 out of the casing 20 and into the needle bore 12 without crushing the pellets 2 and such that the force of ejection does not cause further separation of tissue layers of the animal 3 to any significant degree. As the needle 4 is withdrawn from the animal 2 while the operator holds the trigger 40 in the retracted position, the impeller 50, in response to the force exerted thereon by the air pressure in the low pressure branch 56, pushes the pellets 2 out of the needle bore 12 and into the cavity from which the needle 4 is withdrawn.

Release of the trigger 40 causes the first and second valves 73 and 77 to change condition such that high pressure air is supplied to the air cylinder 45 at the front end 46 thereof and venting the rear end 47 of the cylinder 45 to atmosphere which causes the piston head 49 to advance to the rear of the cylinder 45 retracting the impeller 50 out of the needle bore 12 and the pellet chamber 22 of the aligned casing 20. Release of the 40 trigger 40 also causes the upper and lower pawl tips 90 and 91 to exert an upward force on the respective casings 20 below which they extend, such that when the impeller 50 is retracted from the aligned casing 20, the next successive casing 20 is advanced into axial alignment with the needle 4 and the retracted impeller 50. Windows or openings 99 are formed in the housing 7 and positioned to permit viewing of the pellet casing 20 positioned in axial alignment with the needle 4 and impeller 50 to permit an operator to visually inspect the casing 20. Such visual inspection is helpful to verify that the casing 20 is in proper alignment, that pellets 2 are in the casing 20 or to verify that a connector bead 26 and connector clamp 25 are not positioned therein. If a connector bead 26 and connector clamp 25 are positioned therein, the operator can manually advance the strip 17 to advance the next successive pellet casing 20 into alignment with the needle 4 and impeller 50.

It is foreseen that the conduit assembly 39 could be modified to alternatingly supply pressurized air to the front end 46 and rear end 47 of the air cylinder 45 at the same pressure, preferably at a pressure which minimizes shattering of the pellets 2 or additional damage to the animal tissue during insertion of the pellets 2. However, in an embodiment (not shown) in which the air supply system was configured to alternatingly supply pressurized air to the front and rear of the cylinder at the same pressure, approximately 30 psig, the upward force exerted by the pawl on the casing from which the impeller was being retracted upon release of the trigger, resulted in excessive binding of the impeller within the casing and reduced performance of the implanter. By configuring the conduit assembly 39 of the preferred embodiment to supply pressurized air to the front end 46 of the cylinder 45 at the higher pressure (i.e. 100 psig) during the retraction stroke of the impeller 50, the problems associated with binding are significantly reduced due to the increased force and rate at which the impeller 50 is retracted.

The pneumatic impeller assembly 35 generally functions as a gas motor utilizing pressurized air supplied thereto through the conduit assembly 39 for selectively and alternatingly driving the impeller 50 from a retracted position to an extended position.

It is foreseen that pneumatic motor means could be utilized solely for advancing the impeller from the retracted position to the extended position or vice versa and that other means could be utilized for advancing the impeller through the other stroke. For example, pressurized air could be supplied solely to the front end of the air cylinder with a spring positioned between the piston head and the rear of the cylinder. A normally open valve, operable by the trigger, would control the supply of pressurized air to the cylinder such that pressurized air was normally supplied to cylinder from the front end thereof causing retraction of the impeller against the force of the spring. Closing the valve by squeezing the trigger would cut of the supply of pressurized air to the cylinder from the front end and exhaust the air therein such that the spring acting against the piston head would advance the impeller to an extended position. Similarly, pressurized air could be supplied solely to the cylinder at the rear through a normally closed valve to advance the impeller to an extended position against the biasing force of a spring.

One advantage of using pressurized air to drive the impeller from the retracted to the extended position, as in the preferred embodiment, is that the pressure of the air supplied to the rear of the cylinder can be varied such as through adjustment of the pressure regulator 66 via adjustment knob 67. Varying conditions for use of the implanter may require differences in the force at which the pellets are ejected by the impeller for optimum performance.

It is also foreseen that the apparatus could be modified to use hydraulics to drive and/or retract the impeller.

Alternative Embodiment

Figure 6:
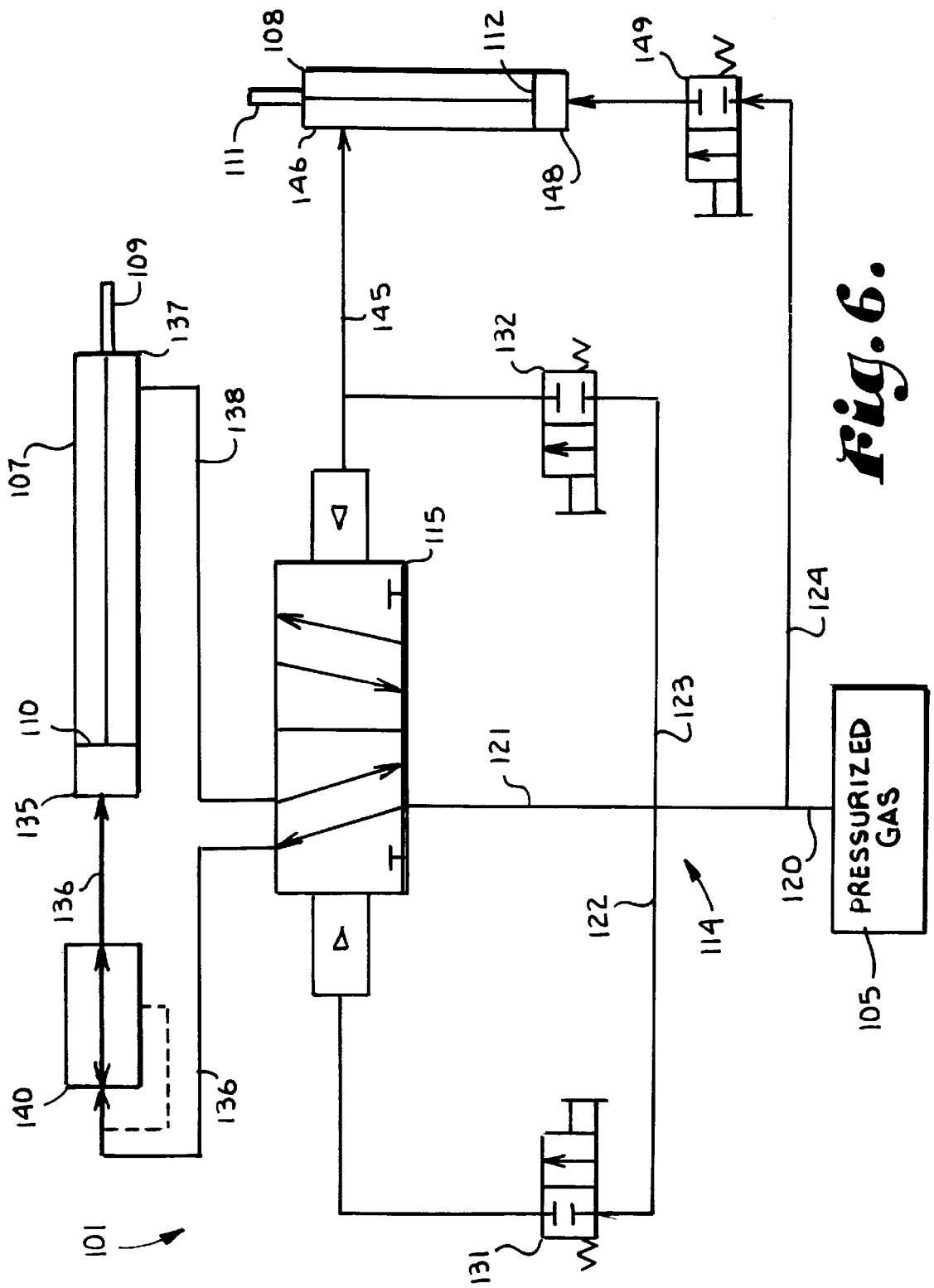
FIG. 6 is a schematic diagram of the pneumatic assembly of an alternative embodiment of the present invention.

FIG. 6 is a schematic diagram of an alternative embodiment of the pneumatic system of a pneumatic veterinary pellet implanter 101. Pressurized gas is supplied to the system at approximately 110 psig through a pressurized gas source 105. The pneumatic system of implanter 101 includes a pellet ejection pneumatic cylinder or first pneumatic cylinder 107 and a magazine advancement pneumatic cylinder or second pneumatic cylinder 108. The first pneumatic cylinder 107 includes a first impeller 109 connected to a first piston head 110 and the second pneumatic cylinder 107 includes a second impeller 111 connected to a second piston head 112. Pressurized gas is supplied to the first and second pneumatic cylinders 107 and 108 from the pressurized gas source 105 through a conduit assembly 114.

A 4-way pneumatic piloted valve 115 controls the flow of pressurized gas to the first pneumatic cylinder 107. A supply line 120 connected to the pressurized gas source 105 is split into four branches, a first branch 121, a second branch 122, a third branch 123 and a fourth branch 124. The first branch 121 is connected to an inlet port of the 4-way valve 115. The second branch 122 and third branch 123 are connected to the 4-way valve 115 for purposes of piloting or toggling the valve 115 between first and second conditions. A first trigger valve 131, which is normally closed, controls the flow of pressurized gas to valve 115 through second branch 122. A second trigger 132, which is also normally closed, controls the flow of pressurized gas to valve 115 through third branch 123.

A rear end 135 of the first pneumatic cylinder 107 is flow connected to the valve 115 by a rear feed branch 136. A front end 137 of the first pneumatic cylinder 107 is flow connected to the valve 115 by a front feed branch 138. The first and second trigger valves 131 and 132 are alternatingly actuated to toggle the valve 115 between the first and second conditions to alternatingly supply pressurized gas to the rear end 135 and front end 137 of the first pneumatic cylinder 107 through rear and front feed branches 136 and 138 respectively.

When the 4-way valve 115 is in the first condition, the first branch 121 of supply line 120 is flow connected to the rear feed branch 136 and the front feed branch 138 is vented to atmosphere. When the 4-way valve 115 is in the second condition, the first branch 121 of supply line 120 is flow connected to the front feed branch 138 and the rear feed branch 136 is vented to atmosphere.

Squeezing or pressing on a trigger mechanism on first trigger valve 131 opens the first trigger valve 131 and supplies a stream of pressurized gas to valve 115 through the second branch 122 which toggles the valve 115 to the first condition. Advancement of the valve to the first condition supplies pressurized gas to the rear end 135 of the first pneumatic cylinder 107 through rear feed branch 136. The pressurized gas supplied to the first pneumatic cylinder 107 through the rear end 135 thereof acts on the first piston head 110 and drives the first impeller 109 to an extended position. The first pneumatic cylinder 107 is mounted within a housing in a manner similar to that discussed above for the preferred embodiment, such that advancement of the first impeller 109 to an extended position advances the first impeller 109 through an aligned magazine casing and needle for ejecting medicinal pellets therethrough.

A regulator 140 is positioned on the rear feed branch 136 and reduces the pressure therein to approximately 30 psig such that pressurized gas is selectively fed to the rear end 135 of first pneumatic cylinder 107 at approximately 30 psig.

Squeezing or pressing on a trigger mechanism on second trigger valve 132 opens the second trigger valve 132 and supplies a stream of pressurized gas to valve 115 through the third branch 123 which toggles the valve 115 to the second condition. Advancement of the valve to the second condition supplies pressurized gas to the front end 137 of the first pneumatic cylinder 107 through front feed branch 138. The pressurized gas supplied to the first pneumatic cylinder 107 through the front end 137 thereof acts on the first piston head 110 and drives the first impeller 109 to a retracted position.

A spur 145 branches off of the third branch 123 downstream of the second trigger valve 132 and extends to a front end 146 of the second pneumatic cylinder 108. Advancement of the second trigger valve 132 to an open condition also supplies pressurized gas to the front end 146 of the second pneumatic cylinder 108, and the pressurized gas entering the cylinder 108 at the front end thereof acts upon the second piston head 112 advancing the second impeller to a retracted condition.

The fourth branch 124 of supply line 120 is flow connected to a rear end 148 of the second pneumatic cylinder 108. A third trigger valve 149, which is also normally closed, is positioned on the fourth branch 124 and controls the flow of pressurized gas therethrough. Squeezing a trigger on the third trigger valve 149, advances the third trigger valve 149 to an open condition thereby supplying pressurized gas to the rear end 148 of the second pneumatic cylinder 108 such that the pressurized gas acts upon the second piston head 112 and advances the second impeller 111 to an extended position.

The second impeller 111 may be connected at a distal end thereof to a magazine advancement mechanism such as the pawl disclosed in the preferred embodiment. In such an arrangement, advancement of the second impeller 111 to an extended position would advance the pawl upward to advance a next successive pellet casing into alignment with the first impeller 109 and the needle. Advancement of the second impeller 111 to the retracted position would pull the pawl downward past the next successive pellet casing, to a cocked position, such that when the second impeller 111 is subsequently advanced to an extended position it advances the next successive pellet casing into alignment with the first impeller 109 and the needle.

Before use of the implanter 101, the first impeller 107 is positioned in the retracted position, and the second impeller is positioned in an extended alignment. A pellet magazine strip is fed into the implanter 101 such that a pellet casing, with pellets therein, is aligned with the first impeller 107. The user inserts the needle into the animal and squeezes the trigger on the first trigger valve 131 which causes the first impeller 107 to advance to the pellets in the aligned pellet casing into the needle. Pressurized air is supplied to the rear end 135 of the first pneumatic cylinder 107 until the user squeezes the trigger on the second trigger valve 132. Therefore as the user removes the needle from the animal (before squeezing the trigger on the second trigger valve 132) the pressurized gas acting on the impeller 107 from the rear end 135 of the cylinder 107 further advances the first impeller to the extended position ejecting the pellets from the needle and into a cavity formed in the animal by the needle.

The user then squeezes the trigger on the second trigger valve 132 which causes retraction of the first impeller 109 and the second impeller 111. The user then squeezes the trigger on the third trigger valve 149 which advances the second impeller 111 to a retracted position to advance the next successive pellet casing into alignment with the first impeller 109 and the needle. The implanter 101 is then ready for the next implantation.

It is to be understood that while certain forms of the present invention have been illustrated and described herein, it is not to be limited to the specific forms or arrangement of parts described and shown.

What is claimed and desired to be secured by letters patent is as follows:

1. An implanter apparatus for implanting a medicinal pellet in an animal comprising:
   (a) an implanter housing having a needle secured on a front end thereof and having a pellet chamber extending behind said needle in axial alignment with a bore of said needle; said pellet chamber adapted for storing a medicinal pellet therein;
   (b) a pneumatic cylinder having an opening in a front end thereof and having a piston including an impeller slidingly secured within said pneumatic cylinder; said impeller advanceable between a retracted position and an extended position relative to said cylinder such that when said impeller is advanced to said extended position said impeller extends through said pellet chamber and through said needle bore;
   (c) a conduit connected at a first end to a source of pressurized gas; said conduit is split into a first branch and a second branch; said first branch connecting said source of pressurized gas to said cylinder proximate a rear end thereof; said second branch connecting said source of pressurized gas to said cylinder proximate said front end thereof;
   (d) a first valve connected to said first branch of said conduit between said source of pressurized gas and said pneumatic cylinder and selectively advanceable between a closed condition wherein a gas flow passageway through said conduit between said source of pressurized gas and said pneumatic cylinder is closed and an open condition wherein said gas flow passageway is open such that pressurized gas entering said pneumatic cylinder at a rear end thereof exerts a force on a rearwardly facing surface of said piston and advances said impeller to said extended position; and
   (e) a second valve connected to said second branch of said conduit between said pressurized gas source and said pneumatic cylinder; said second valve selectively advanceable between an open condition wherein a gas flow passageway through said second branch is open, and a closed condition wherein said gas flow passageway through said second branch is closed; said second valve connected to said first valve such that advancing said second valve to said open condition advances said first valve to said closed condition such that pressurized gas entering said front end of said pneumatic cylinder through said second branch exerts a force on a forwardly facing surface of said piston and advances said impeller to said retracted position; advancement said second valve to said closed condition advances said first valve to said open condition such that pressurized gas entering said rear end of said pneumatic cylinder through said first branch advances said impeller to said extended position.

2. The implanter as in claim 1 further comprising:
   (a) a pressure reducing regulator positioned on said first branch and reducing said pressure in said first branch downstream thereof to a selected pressure.

3. The improved implanter apparatus as in claim 2 further including:
   (a) a trigger on said implanter housing and advanceable between an extended position and a retracted positions, said trigger positioned proximate said second valve such that advancement of said trigger to said retracted position closes said second valve and advancement of said trigger to said extended position opens said second valve.

4. The improved implanter apparatus as in claim 3 wherein:
   (a) said pellet chamber comprises one of a plurality of pellet chambers formed in a pellet magazine strip; and
   (b) said implanter further includes a pawl connected at a first end to said trigger and engaging said pellet magazine strip at a second end such that advancement of said trigger to said retracted position advances said pawl past a next pellet chamber and advancement of said trigger from said retracted position to said extended position advances said next pellet chamber into axial alignment with said impeller and said needle bore.

5. An implanter apparatus for implanting a medicinal pellet in an animal comprising:
   (a) an implanter housing having a needle secured on a front end thereof and having a pellet magazine slot formed therein;
   (b) a pellet magazine including a plurality of pellet chambers formed therein and adapted for storing a medicinal pellet therein; said pellet magazine slidingly securable within said pellet magazine slot such that successive pellet chambers are advanceable into axial alignment with a bore of said needle;
   (c) a pneumatic cylinder having a piston including an impeller slidingly secured within said pneumatic cylinder; said impeller advanceable between a retracted position and an extended position relative to said cylinder such that when said impeller is advanced to said extended position said impeller extends through said pellet chamber aligned with said needle bore and through said needle bore;
   (d) a conduit assembly having a trunk line connected to a source of pressurized gas; said conduit assembly having a first branch connected at one end to said trunk line and at a second end to said pneumatic cylinder proximate a rear end thereof; said conduit assembly having a second branch connected at one end to said trunk line and at a second end to said pneumatic cylinder proximate a front end thereof;
   (e) a first valve connected to said first branch between said source of pressurized gas and said pneumatic cylinder and selectively advanceable between a closed condition wherein a first gas flow passageway through said first branch between said source of pressurized gas and said rear end of said pneumatic cylinder is closed and an open condition wherein said first gas flow passageway is open such that pressurized gas entering said pneumatic cylinder at said rear end thereof exerts a force on a rearwardly facing surface of said piston and advances said impeller to said extended position;
   (f) a second valve connected to said second branch of between said pressurized gas source and said front end of said pneumatic cylinder; said second valve selectively advanceable between an open condition wherein a second gas flow passageway through said second branch is open, and a closed condition wherein said second gas flow passageway through said second branch is closed; said second valve connected to said first valve such that advancing said second valve to said open condition advances said first valve to said closed condition such that pressurized gas entering said front end of said pneumatic cylinder through said second branch exerts a force on a forwardly facing surface of said piston and advances said impeller to said retracted position; advancement said second valve to said closed condition advances said first valve to said open condition such that pressurized gas entering said rear end of said pneumatic cylinder through said first branch advances said impeller to said extended position; and (g) a trigger on said implanter housing advanceable between an extended position and a retracted positions, said trigger selectively engaging said second valve such that advancement of said trigger to said retracted position closes said second valve and advancement of said trigger to said extended position opens said second valve.

6. The implanter as in claim 5 further comprising:

(a) a pressure reducing regulator positioned on said first branch and reducing said pressure in said first branch downstream thereof to a selected pressure.

7. The implanter as in claim 5 further comprising:

(a) a pawl connected at a first end to said trigger and engaging said pellet magazine at a second end such that advancement of said trigger to said retracted position advances said pawl past a next pellet chamber and advancement of said trigger from said retracted position to said extended position advances said next pellet chamber into axial alignment with said impeller and said needle bore.

8. An implanter apparatus for implanting a medicinal pellet in an animal comprising:

(a) an implanter housing having a needle secured on a front end thereof;

(b) a pellet casing having pellet chamber formed therein adapted for storing a medicinal pellet therein, said pellet casing positioned within said implanter housing behind said needle such that said pellet chamber extends in axial alignment with a bore of said needle;

(c) a pneumatic cylinder having a piston including an impeller slidingly secured within said pneumatic cylinder; said impeller advanceable between a retracted position and an extended position relative to said cylinder such that when said impeller is advanced to said extended position said impeller extends through said pellet chamber aligned with said needle bore and through said needle bore; and (d) means for alternatingly supplying pressurized gas to a front end of said pneumatic cylinder at a first pressure for advancing said impeller to said retracted position and to a rear end of said pneumatic cylinder at a second pressure for advancing said impeller to said extended position.

9. The implanter as in claim 8 wherein:

(a) said second pressure is lower than said first pressure.

10. The implanter as in claim 8 wherein said pellet casing comprises one of a plurality of pellet casings each having a pellet chamber formed therein and secured together to form a pellet magazine strip, said implanter further comprising;

(a) means for advancing a next successive pellet chamber into axial alignment with said needle bore upon advancement of said impeller from said extended position to said retracted position.

11. An implanter apparatus for implanting a pellet in an animal comprising:

(a) an implanter housing having a needle secured on a front end thereof and having a pellet chamber adapted for receiving a pellet therein; said pellet chamber positioned within said implanter housing behind said needle such that said pellet chamber extends in axial alignment with a bore of said needle;

(b) a pneumatic cylinder having a piston including an impeller slidingly secured within said pneumatic cylinder; said impeller advanceable between a retracted position and an extended position relative to said cylinder such that when said impeller is advanced to said extended position said impeller extends through said pellet chamber and through said needle bore;

(c) a conduit assembly having a trunk line connected to a source of pressurized gas; said conduit assembly having a first branch connected at one end to said trunk line and at a second end to said pneumatic cylinder proximate a rear end thereof, said conduit assembly having a second branch connected at one end to said trunk line and at a second end to said pneumatic cylinder proximate a front end thereof;

(d) a valve assembly selectively controlling the flow of pressurized gas from said source of pressurized through said first branch to said rear end of said pneumatic cylinder or through said second branch to said front end of said pneumatic cylinder; and (e) a pressure reducer connected to said first branch and reducing a pressure of said pressurized gas in said first branch downstream of said pressure reducer.

12. The implanter apparatus as in claim 11 wherein said valve assembly comprises:

(a) a first valve connected to said first branch and selectively advanceable between a closed condition wherein a gas flow passageway through said first branch is closed and an open condition wherein said gas flow passageway through said first branch is open;

(b) a second valve connected to said second branch and selectively advanceable between an open condition wherein a gas flow passageway through said second branch is open and a closed condition wherein a gas flow passageway through said second branch is closed;

(c) said first valve is air piloted and is connected to said second valve by a spur of said conduit assembly extending from said second branch, downstream of said second valve, to said first valve, such that advancement of said second valve to said open condition causes said air piloted first valve to advance to a closed condition and advancement of said second valve to said closed condition causes said air piloted first valve to advance to an open position.

* * * * *